US010322259B2

United States Patent
Stoneman et al.

(10) Patent No.: US 10,322,259 B2
(45) Date of Patent: Jun. 18, 2019

(54) SYSTEMS AND METHODS FOR MITIGATING MOTION SICKNESS IN A VEHICLE

(71) Applicant: GM Global Technology Operations LLC, Detroit, MI (US)

(72) Inventors: Olivia Stoneman, Shelby Township, MI (US); Cristin L. Colling, Belleville, MI (US); Marlow D. Hudson, Troy, MI (US); Alexander Rivera, Sterling Heights, MI (US)

(73) Assignee: GM GLOBAL TECHNOLOGY OPERATIONS LLC, Detroit, MI (US)

( * ) Notice: Subject to any disclaimer, the term of this patent is extended or adjusted under 35 U.S.C. 154(b) by 67 days.

(21) Appl. No.: 15/614,070

(22) Filed: Jun. 5, 2017

(65) Prior Publication Data

US 2018/0344969 A1    Dec. 6, 2018

(51) Int. Cl.
*A61M 21/02* (2006.01)
*A61B 5/00* (2006.01)
*A61N 1/36* (2006.01)

(52) U.S. Cl.
CPC ........... *A61M 21/02* (2013.01); *A61B 5/4005* (2013.01); *A61N 1/3606* (2013.01)

(58) Field of Classification Search
None
See application file for complete search history.

(56) References Cited

U.S. PATENT DOCUMENTS

| 7,983,761 | B2 | 7/2011 | Giuntoli et al. | |
|---|---|---|---|---|
| 2002/0066392 | A1* | 6/2002 | Calam | B60R 11/0252 108/33 |
| 2007/0034212 | A1* | 2/2007 | Brendley | A61M 21/00 128/897 |
| 2007/0173908 | A1* | 7/2007 | Begnaud | A61N 1/36025 607/63 |
| 2011/0140475 | A1* | 6/2011 | Spitler | B60R 7/04 296/37.8 |
| 2013/0070043 | A1* | 3/2013 | Geva | B60K 28/066 348/14.02 |

OTHER PUBLICATIONS

U.S. Appl. No. 15/654,287, filed Jul. 19, 2017, Wan et al.

* cited by examiner

*Primary Examiner* — Ankit D Tejani

(57) ABSTRACT

An example system for mitigating motion sickness within a vehicle is provided. The system includes a motion sickness mitigation device (MSMD) integrated into the vehicle and configured to generate electrical stimulation pulses upon actuation. The system also includes a controller operatively connected to the MSMD. The controller is configured to: obtain signals indicative of a potential motion sickness condition; determine whether a motion sickness conditions exists based on the signals; and, in response to determining that a motion sickness condition exists, actuate the MSMD.

7 Claims, 12 Drawing Sheets

SYSTEMS AND METHODS FOR MITIGATING MOTION SICKNESS IN A VEHICLE

INTRODUCTION

The information provided in this section is for the purpose of generally presenting the context of the disclosure. Work of the presently named inventors, to the extent it is described in this section, as well as aspects of the description that may not otherwise qualify as prior art at the time of filing, are neither expressly nor impliedly admitted as prior art against the present disclosure.

The present disclosure relates generally to vehicles and, more particularly, to an in-vehicle system for mitigation motion sickness.

Motion sickness is a condition in which a disagreement exists between visually perceived movement and the vestibular system's sense of movement. Depending on the cause, it can also be referred to as seasickness, car sickness, simulation sickness or airsickness. Motion sickness is a fairly common condition, with some reports estimating that nearly one in four people have experienced motion sickness while in an automobile.

Research indicates that people are nearly twice as likely to experience motion sickness while traveling in an autonomous vehicle as compared to traveling in a human-operated vehicle. Accordingly, systems and methods for mitigating motion sickness in vehicular occupants are desired.

SUMMARY

In a feature, a system is provided. The system includes a motion sickness mitigation device (MSMD) integrated into a vehicle and configured to generate electrical stimulation pulses upon actuation. The system also includes a controller operatively connected to the MSMD. The controller is configured to: obtain signals indicative of a potential motion sickness condition; determine whether a motion sickness conditions exists based on the signals; and, in response to determining that a motion sickness condition exists, actuate the MSMD.

In a feature, the system also includes the one or more motion sickness detectors, which are operatively connected to the controller. The one or more motion sickness detectors may be configured to generate the signals indicative of the potential motion sickness condition. In one example of the foregoing feature, the one or more motion sickness detectors includes at least one of: a galvanic skin cell sensor; an electroencephalogram (EEG) sensor; an accelerometer; a speed sensor; a yaw-rate sensor; a tilt-sensor; a GPS system; a clock; a navigation system; and a weather forecast system.

In one feature, the controller is configured to determine whether the motion sickness condition exists by at least one of: determining that a vehicle occupant is currently experiencing motion sickness; and determining that the vehicle occupant is likely to experience motion sickness in the future.

In another feature, the vehicle may include an automobile. In this feature, the MSMD may be integrated into at least one of: a seatbelt; an armrest; a center console; and an interior door panel. In one example of this feature, the MSMD is integrated into the seatbelt, and the MSMD is slidably adjustable about a length of the seatbelt. In another example of this feature, the MSMD is integrated into the seatbelt, and the MSMD is woven into fabric of the seatbelt. In still another example of this feature, the MSMD is integrated into the armrest or center console, and the armrest or center console includes a protective sleeve adjustable between a first position that renders the MSMD accessible for therapy and a second position that renders the MSMD inaccessible for therapy. In yet another example of this feature, the MSMD is integrated into the armrest or center console, and the armrest or center console includes a flip cover adjustable between a first position that renders the MSMD accessible for therapy and a second position that renders the MSMD inaccessible for therapy. In another example of this feature, the MSMD is integrated into the center console, and the center console includes at least one of: a front center console and a rear center console. In yet another example of this feature, the MSMD is integrated into the interior door panel, and the MSMD is integrated into a face plate of the interior door panel.

In one feature, the MSMD includes electrical stimulation adjustment buttons configured to adjust at least one of: an intensity level of the electrical stimulation pulses and a frequency of the electrical stimulation pulses.

In another feature, the vehicle includes an airplane, and the MSMD is integrated into an armrest of the airplane. In one example of the foregoing feature, the controller is configured to determine whether the motion sickness condition exists by detecting, based on the signals, at least one of the following: the airplane is taking off; the airplane is landing; the airplane is experiencing turbulence; and the airplane is likely to experience turbulence.

In a feature, the vehicle includes a train, and the MSMD is integrated into an armrest of the train. In one example of the foregoing feature, the controller is configured to determine whether the motion sickness condition exists by detecting, based on the signals, at least one of the following: train speed; scheduled stops and starts associated with the train's route; and known curve's in the train's route.

In another feature, the vehicle includes a boat, and the MSMD is integrated into an armrest of the boat. In one example of the foregoing feature, the controller is configured to determine whether the motion sickness condition exists by detecting, based on the signals, at least one of the following: a weather forecast including wave heights and wind speed; boat speed; and boat acceleration.

In one feature, a system is provided. The system may include a motion sickness mitigation device (MSMD) integrated into a seatbelt of a vehicle and configured to generate electrical stimulation pulses upon actuation. The system may also include a controller operatively connected the MSMD. The controller may be configured to: obtain signals indicative of a potential motion sickness condition; determine whether a motion sickness condition exists based on the signals; and, in response to determining that a motion sickness condition exists, actuate the MSMD.

In another feature, a system is provided. The system may include a motion sickness mitigation device (MSMD) integrated into at least one of an armrest and center console of a vehicle and configured to generate electrical stimulation pulses upon actuation. The system may also include a controller operatively connected the MSMD. The controller may be configured to: obtain signals indicative of a potential motion sickness condition; determine whether a motion sickness condition exists based on the signals; and, in response to determining that a motion sickness condition exists, actuate the MSMD.

Further areas of applicability of the present disclosure will become apparent from the detailed description, the claims and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings, wherein.

In the drawings, reference numbers may be reused to identify similar and/or identical elements.

DETAILED DESCRIPTION

Figure 1:
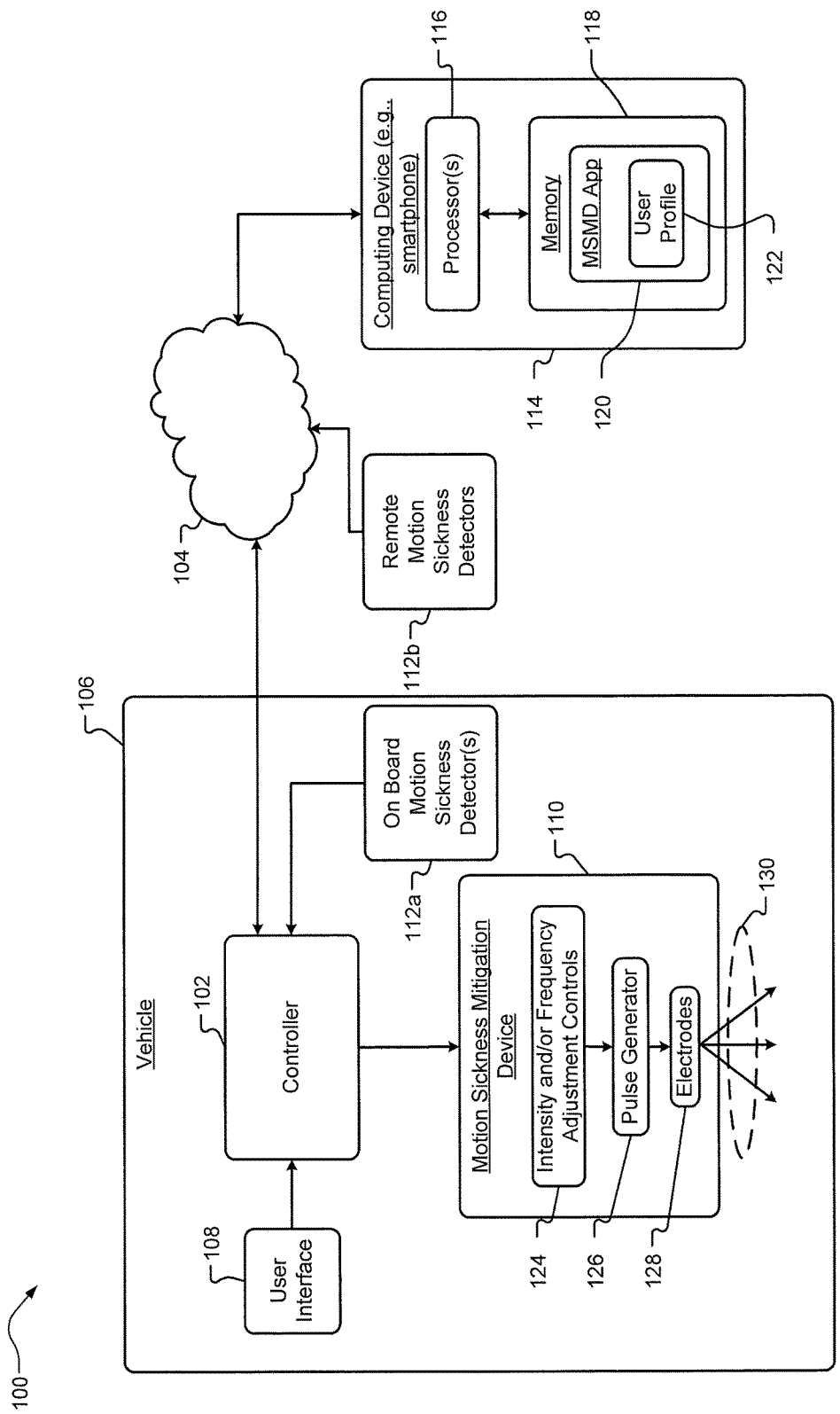
FIG. 1 is a functional block diagram of an example system for mitigating motion sickness in a vehicle.

Referring now to FIG. 1, a system 100 for mitigating motion sickness in a vehicle is shown. The system 100 includes a vehicle 106. The vehicle 106 may include, but is not limited to, an automobile, airplane, train, boat, etc. In some examples, the system 100 includes one or more remote motion sickness detectors 112*b* and/or a computing device 114 in communication with the vehicle 106 over a network 104.

The one or more remote motion sickness detectors 112*b* may include any suitable devices and/or systems for generating signals indicative of an existing or potential motion sickness condition. By way of example and not limitation, the remote motion sickness detector(s) 112*b* may include weather forecast systems (e.g., weather systems configured to detect conditions such as wave heights, wind speed, turbulence, precipitation, etc.), navigation or route monitoring systems (e.g., navigation or route monitoring systems configured to detect a vehicle's location in relation to a known path), etc.

The computing device 114 may include any suitable device having one or more processors 116 and memory 118 configured to execute one or more applications to assist in motion sickness mitigation. The computing device may include, but is not limited to, a smartphone, a mobile phone, a tablet, a laptop, a desktop, etc. In some examples, the memory 118 includes an executable MSMD application 120, which may be used to control a motion sickness mitigation device (MSMD) 110 integrated into the vehicle 106. Furthermore, in some examples, the MSMD application 120 may include a user profile 122 including details concerning a vehicle occupant to allow, among other things, customization of motion sickness mitigation therapy via the MSMD application 120 based on the occupant's attributes and preferences.

The network 104 may include a local area network (LAN), a wide area network (WAN) such as the Internet, or other type of network.

The vehicle 106 includes a controller 102, a user interface 108, one or more on board motion sickness detectors 112*a* and an integrated motion sickness mitigation device (MSMD) 110. The architecture of the controller 102 is described in greater detail with regard to FIG. 2 below however, briefly, the controller 102 includes suitable logic to control operation of the MSMD 110 based on, for example, input from the on board motion sickness detector(s) 112*a*, remote motion sickness detectors 112*b*, and/or MSMD app 120.

The user interface 108 may include, but is not limited to, a digital display and controlling logic integrated into the vehicle 106 (e.g., in the vehicle dash in the case of an automobile or boat, or in the back of a seat in the case of an airplane or train). As discussed in additional detail below, according to certain examples, the user interface 108 may obtain input from a vehicle occupant to influence control over the MSMD 110 and/or generate output to assist a vehicle occupant in utilizing the MSMD 110.

The on board motion sickness detector(s) 112*a* may include any suitable devices and/or systems for generating signals indicative of an existing or potential motion sickness condition. By way of example and not limitation, on board motion sickness detector(s) 112*a* may include one or more of a galvanic skin cell sensor (e.g., to detect symptoms of motion sickness such as increased body temperature or sweating of an occupant), an electroencephalogram (EEG) sensor (e.g., to detect brain waves associated with an occupant experiencing motion sickness), an accelerometer (e.g., to detect vehicle dynamics known to cause motion sickness), a speed sensor (e.g., to detect vehicle dynamics known to cause motion sickness), a yaw-rate sensor (e.g., to detect vehicle dynamics known to cause motion sickness), a tilt-sensor (e.g., to detect vehicle dynamics known to cause motion sickness) a GPS system (e.g., to detect whether the vehicle is traveling along a path likely to induce motion sickness), and a clock (e.g., to detect whether the vehicle 106 is likely to be at a location known to induce motion sickness, for example, because the vehicle's route is predetermined).

The MSMD 110 may include any suitable device capable of generating electrical stimulation pulses 130, which are known to mitigate symptoms of motion sickness when applied, for example, to the ventral side of a vehicle occupant's wrist. In one example, the MSMD 110 may include an electro-acupuncture device.

The MSMD 110 includes a pulse generator 126 and electrodes 128. The pulse generator 126, which may be powered by any suitable energy source, such as the vehicle's battery (not shown), is configured to provide electrical stimulation pulses to the electrodes 128. The electrodes 128 are configured to transfer the electrical stimulation pulses 130 to a vehicle occupant's skin in order to provide motion sickness mitigation therapy. In some examples, the MSMD 110 may include two half-moon shaped electrodes separated by a non-conducting material (e.g., plastic), as shown in FIGS. 3-6 and 8-10. However, those having ordinary skill in the art will appreciate that the electrodes 128 may take on any suitable configuration for transmitting the electrical stimulation pulses 130 to a vehicle occupant without deviating from the teachings herein.

In some examples, the MSMD 110 also includes intensity and/or frequency adjustment controls 124. The intensity and/or frequency adjustment controls 124 may include any suitable controls for adjusting the intensity and/or frequency of the electrical stimulation pulses 130, such as buttons, knobs, etc. In one example, the intensity and/or frequency adjustment controls 124 may include a micro switch configured to detect pressure applied to the electrodes 128 and adjust the intensity and/or frequency of the electrical stimulation pulses 130 based on the detected pressure (e.g., pressure applied by an occupant pressing their wrist against the electrodes 128). In another example, the intensity and/or frequency adjustment controls 124 may include a microphone and suitable logic for registering and responding to voice commands.

In operation, the system 100 may function as follows. The controller 102 is configured to obtain (i.e., fetch or receive) signals indicative of a potential motion sickness condition. The signals may be generated by, and obtained from the on board motion sickness detector(s) 112b and/or the remote motion sickness detector(s) 112b according to some examples of the present disclosure. The controller 102 is configured to determine whether a motion sickness condition exists based on the signals. In one example, determining whether a motion sickness condition exists may include determining whether a signal value (e.g., a value indicating vehicular acceleration, speed, tilt, wave height, wind speed, turbulence, angle of a turn, angle of an ascent or decline, etc.) exceeds a predetermined threshold. In a further example, the controller 102 may be configured to determine if a motion sickness condition exists by determining that a vehicle occupant is currently experiencing motion sickness (e.g., based on readings from a galvanic skin cell sensor and/or EEG sensor). In yet another example, the controller 102 may be configured to determine if a motion sickness condition exists by determining that a vehicle occupant is likely to experience motion sickness in the future (e.g., based on readings from weather forecast systems and/or navigation/route monitoring systems).

In response to determining that a motion sickness condition exists, the controller 102 is configured to actuate the MSMD 110. Actuating the MSMD 110 causes the pulse generator 126 to generate electrical stimulation pulses 130 which may be transmitted to a vehicle occupant via the electrodes 128 to provide motion sickness relief.

In some examples, actuation of the MSMD 110 may be based on user input from, for example, a vehicle occupant. For example, in some implementations, the user interface 108 may receive input (e.g., via a user touching a touch-sensitive screen of the interface 108). The input may be processed by the controller 102 and used to control operation of the MSMD 110. In other implementations, a user may input operational instructions for the MSMD 110 via the MSMD application 120 (e.g., via a user touching a touch-sensitive screen of the computing device 114).

With continued regard to the MSMD application 120, according to some examples, the MSMD application 120 may be configured to perform one or more of the following functions: (i) reminding the user/occupant that the MSMD 110 is available for their use (e.g., if the user/occupant has not made use of the MSMD 110 for a predetermined amount of time); (ii) providing feedback on historical use information (i.e., ratio of "in use," "not in use," cycle time of use, how hard the system has been working, etc.); (iii) calculating a route of the vehicle (e.g., through crowdsourcing); (iv) providing instructions on using the MSMD 110; (v) adjusting the intensity and/or frequency of electrical stimulation pulses 130; (vi) turning the MSMD 110 on/off; (vii) performing machine-learning (supervised or unsupervised) to understand historical use patterns and predictively adjusting operation of the MSMD 110 based on the machine learning; (viii) etc.

Figure 2:
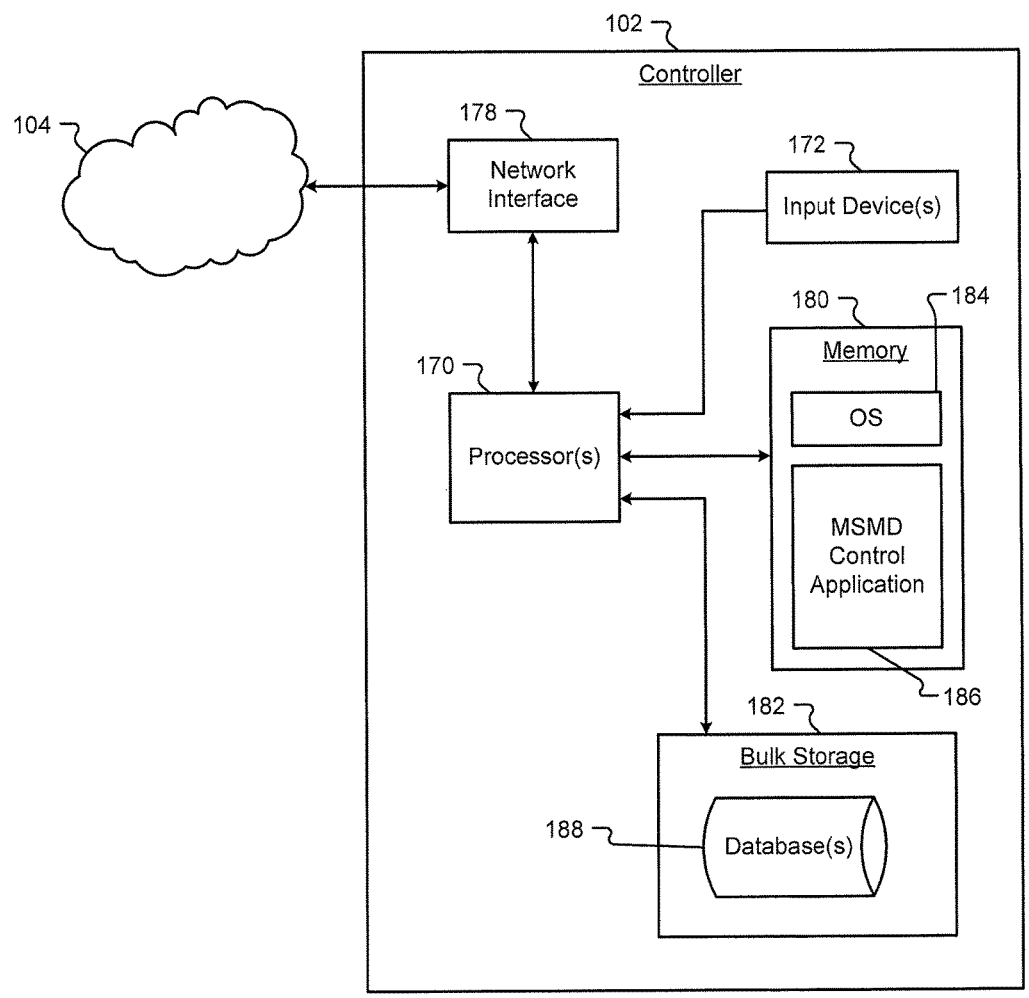
FIG. 2 is a functional block diagram of an example controller configured to control a motion sickness mitigation device.

Turning now to FIG. 2, one example of the controller 102 for controlling the MSMD 110 is shown. The controller 102 includes one or more CPUs or processors 170, input device(s) 172, a network interface 178, a memory 180, and a bulk storage 182.

The network interface 178 connects the controller 102 to ancillary components including, for example, the on board motion sickness detector(s) 112a, the remote motion sickness detector(s) 112b, the computing device 114, etc. via the network 104. For example, the network interface 178 may include a wired interface (e.g., an Ethernet interface) and/or a wireless interface (e.g., a Wi-Fi, Bluetooth, near field communication (NFC), or other wireless interface). The memory 180 may include volatile or nonvolatile memory, cache, or other type of memory. The bulk storage 182 may include flash memory, one or more hard disk drives (HDDs), or other bulk storage device.

The processor 170 of the computing device 102 executes an operating system (OS) 184 and a MSMD control application 186 configured to control operation of the MSMD. The bulk storage 182 may store one or more databases 188 that store data structures used by the MSMD control application 186 to perform respective functions.

FIGS. 3-10 illustrate various exemplary ways in which the MSMD 110 may be integrated into a variety of different vehicle types.

Figure 3:
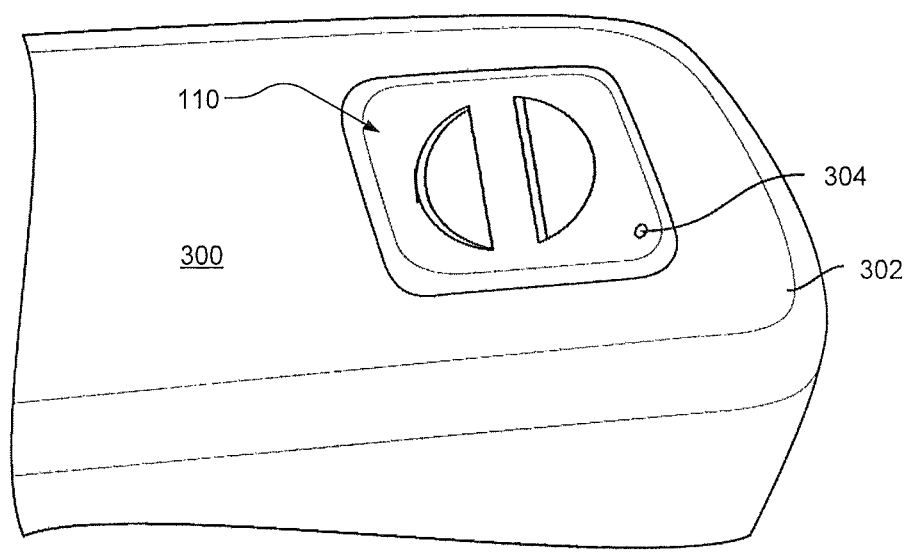
FIG. 3 is a perspective view of an example armrest of an automobile including a motion sickness mitigation device.

With reference to FIG. 3, an example implementation of the MSMD 110 integrated into an armrest 300 of an automobile is shown. More specifically, the MSMD 110 is integrated into soft trim 302 of the armrest 300, and includes a bezel 304.

Figure 4:
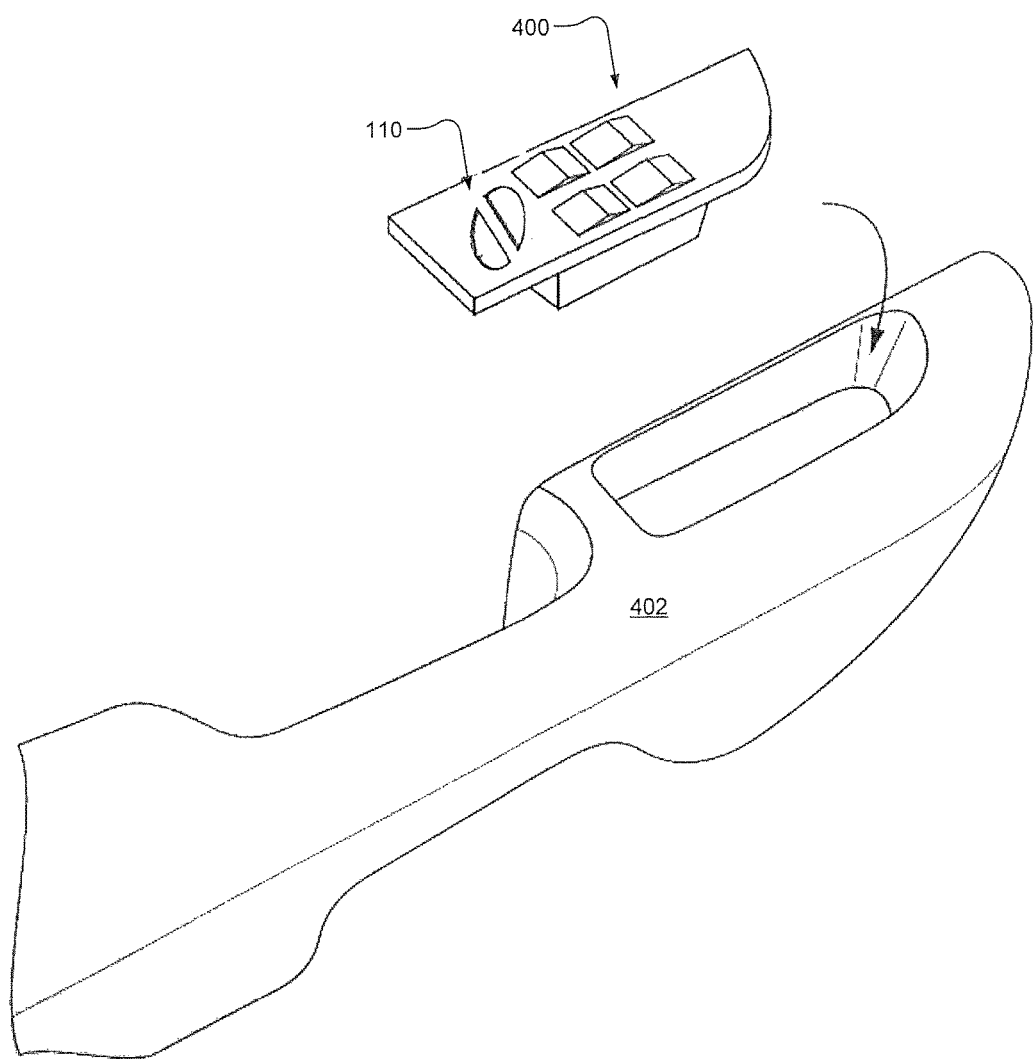
FIG. 4 is an exploded perspective view of an example face plate of a door panel of an automobile including a motion sickness mitigation device.

With reference to FIG. 4, an example implementation of the MSMD 110 integrated into a face plate 400 of a door panel 402 of an automobile is shown.

Figure 5:
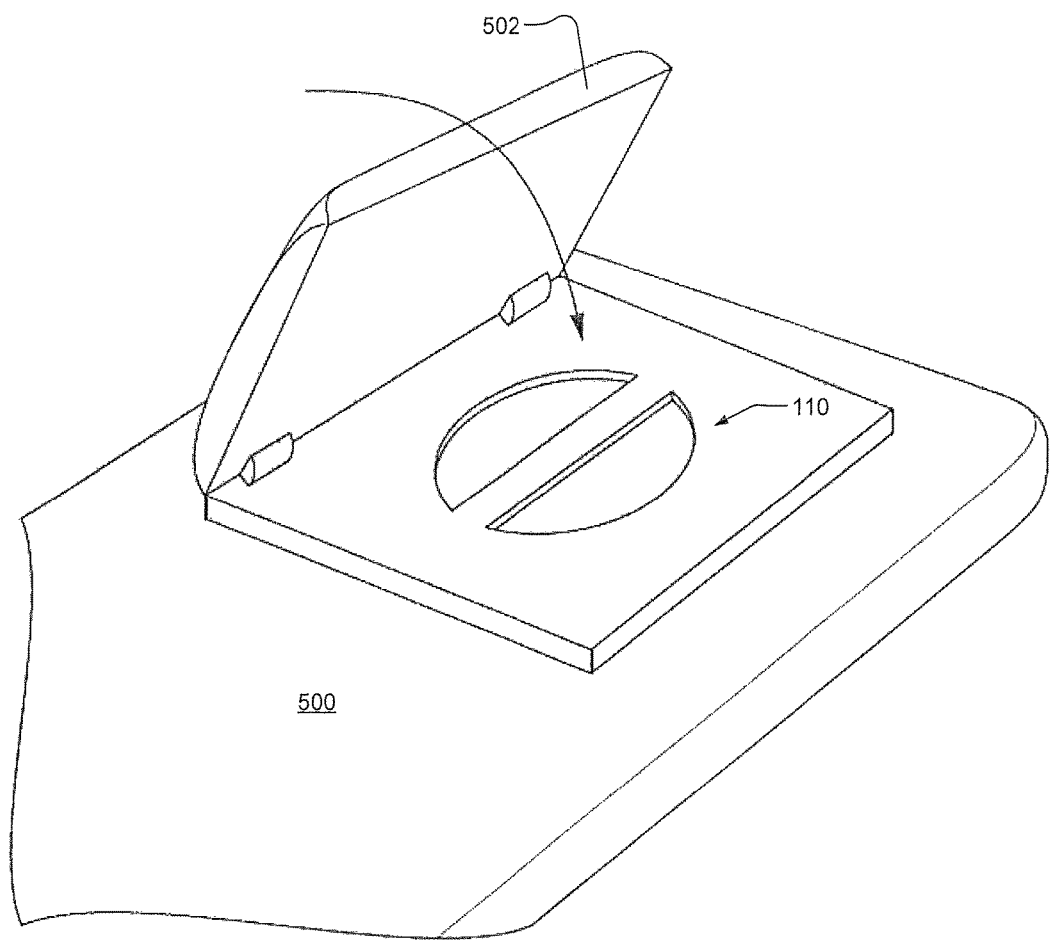
FIG. 5 is a perspective view of an example center console of an automobile including a motion sickness mitigation device.

With reference to FIG. 5, an example implementation of the MSMD 110 integrated into an armrest/center console 500 of an automobile is shown. In addition, according to this example, the armrest/center console 500 includes a flip cover 502 adjustable between a first (e.g., "open") position that renders the MSMD 110 accessible for therapy and a second (e.g., "closed") position that renders the MSMD 110 inaccessible for therapy. Although FIG. 5 only illustrates a flip cover 502 for rendering the MSMD 110 accessible/inaccessible for therapy, in another example, a protective sleeve adjustable between first and second positions may be used instead of the flip cover 502 to render the MSMD 110 accessible/inaccessible for therapy. In an example, where 500 constitutes a center console, it may include a front or rear center console. In addition, in some examples, the MSMD 110 may be oriented differently than the orientation shown in FIG. 5. For example, in some implementations, the MSMD 110 may be rotated 90 degrees (either clockwise or counterclockwise) from the orientation depicted in FIG. 5.

Figure 6:
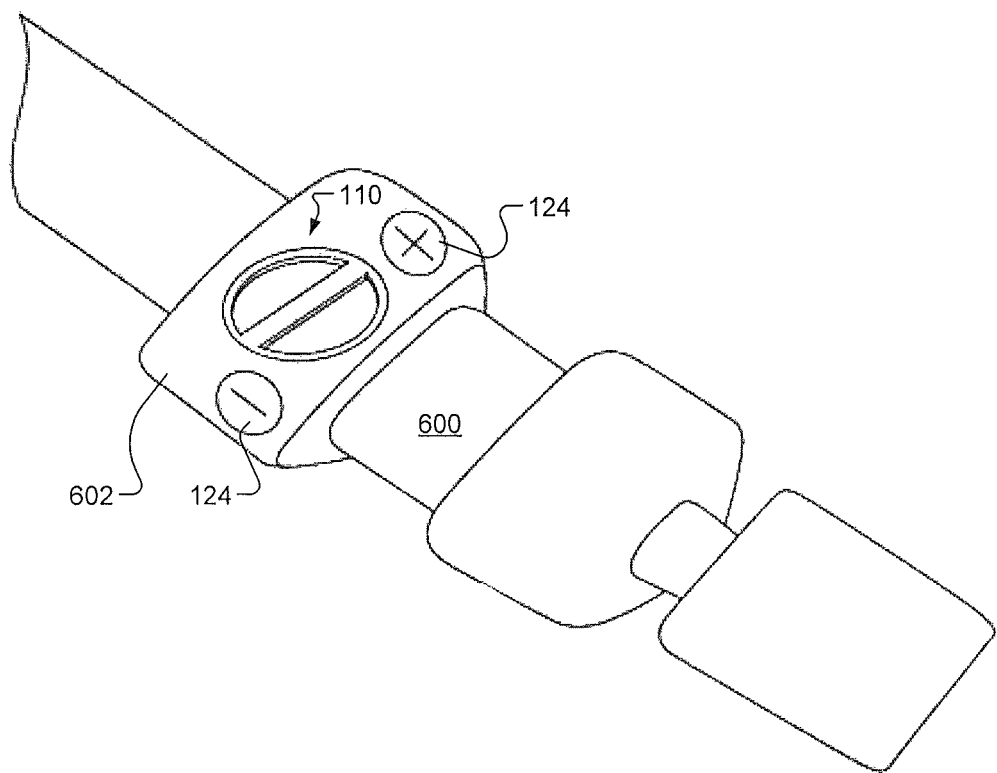
FIG. 6 is a perspective view of an example seat belt of an automobile including a slidably adjustable motion sickness mitigation device.

With reference to FIG. 6, an example implementation of the MSMD 110 integrated into a seatbelt 600 of an automobile is shown. In this example, the MSMD 110 is slidably adjustable about the length of the seatbelt 600 by virtue of a sliding member 602. The sliding member 602 is configurable between a first, sliding state in which it may be moved a about the length of the seatbelt 600 and a second, locked state in which it is locked in place. Any suitable mechanisms known in the art for sliding and locking the sliding member 602 may be employed without deviating from the teachings herein. In addition, in this example, MSMD 110 includes intensity and/or frequency adjustment controls 124 in the form of buttons.

Figure 7:
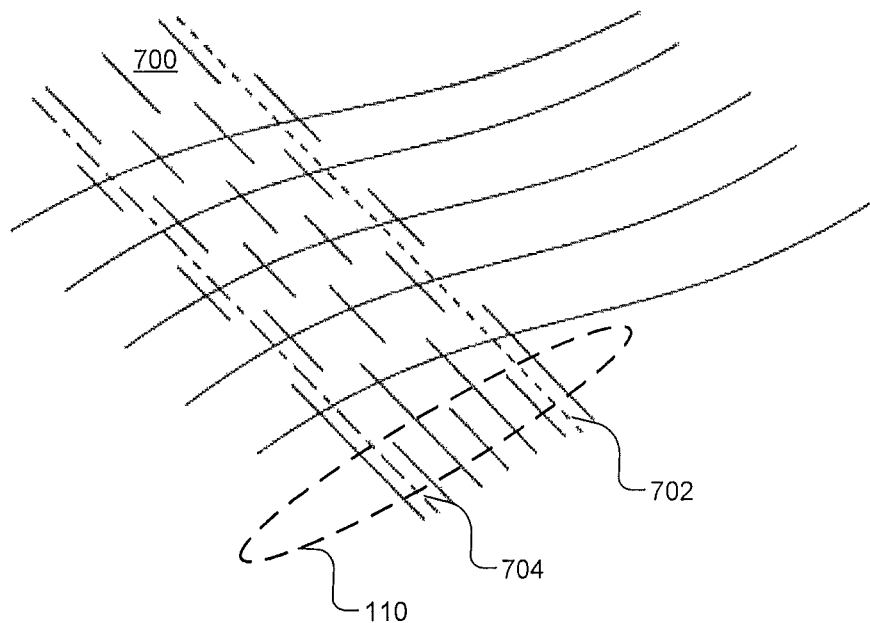
FIG. 7 is a perspective view of an example seat belt of an automobile including an interwoven motion sickness mitigation device.

Referring now to FIG. 7, another example implementation of the MSMD 110 integrated into a seatbelt 700 of an automobile is shown. In this example, the electrodes of the MSMD 110 take the form of a positive terminal 702 and a negative terminal 704 woven or knitted into the fabric of the seat belt 700.

Figure 8:
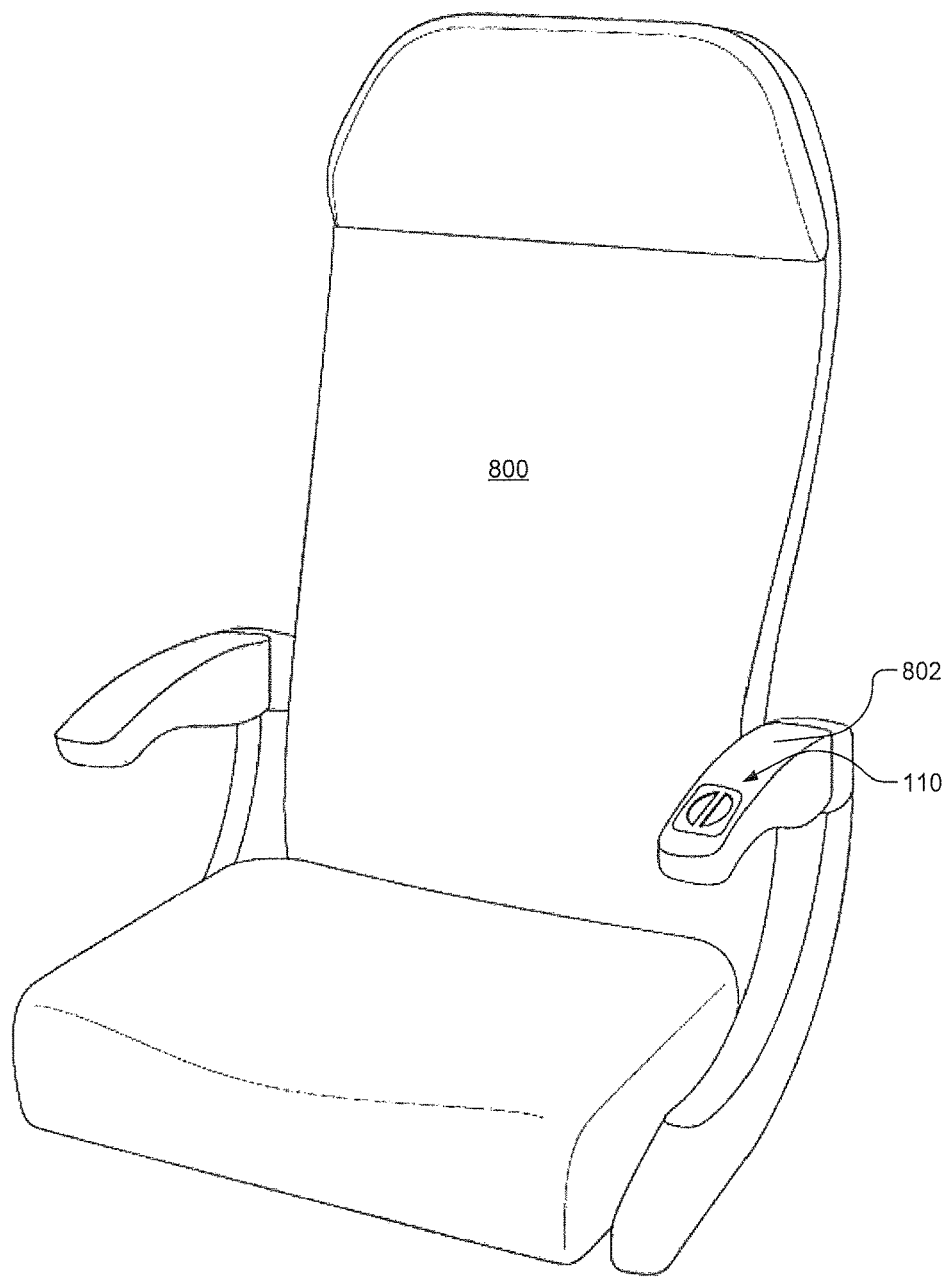
FIG. 8 is a perspective view of an example airplane seat including a motion sickness mitigation device integrated into the armrest.

Referring now to FIG. 8, an example implementation of the MSMD 110 integrated into an armrest 802 of an airplane seat 800 is shown. In some examples, the MSMD 110 may be oriented differently than the orientation shown in FIG. 8. For example, in some implementations, the MSMD 110 may be rotated 90 degrees (either clockwise or counterclockwise) from the orientation depicted in FIG. 8.

Figure 9:
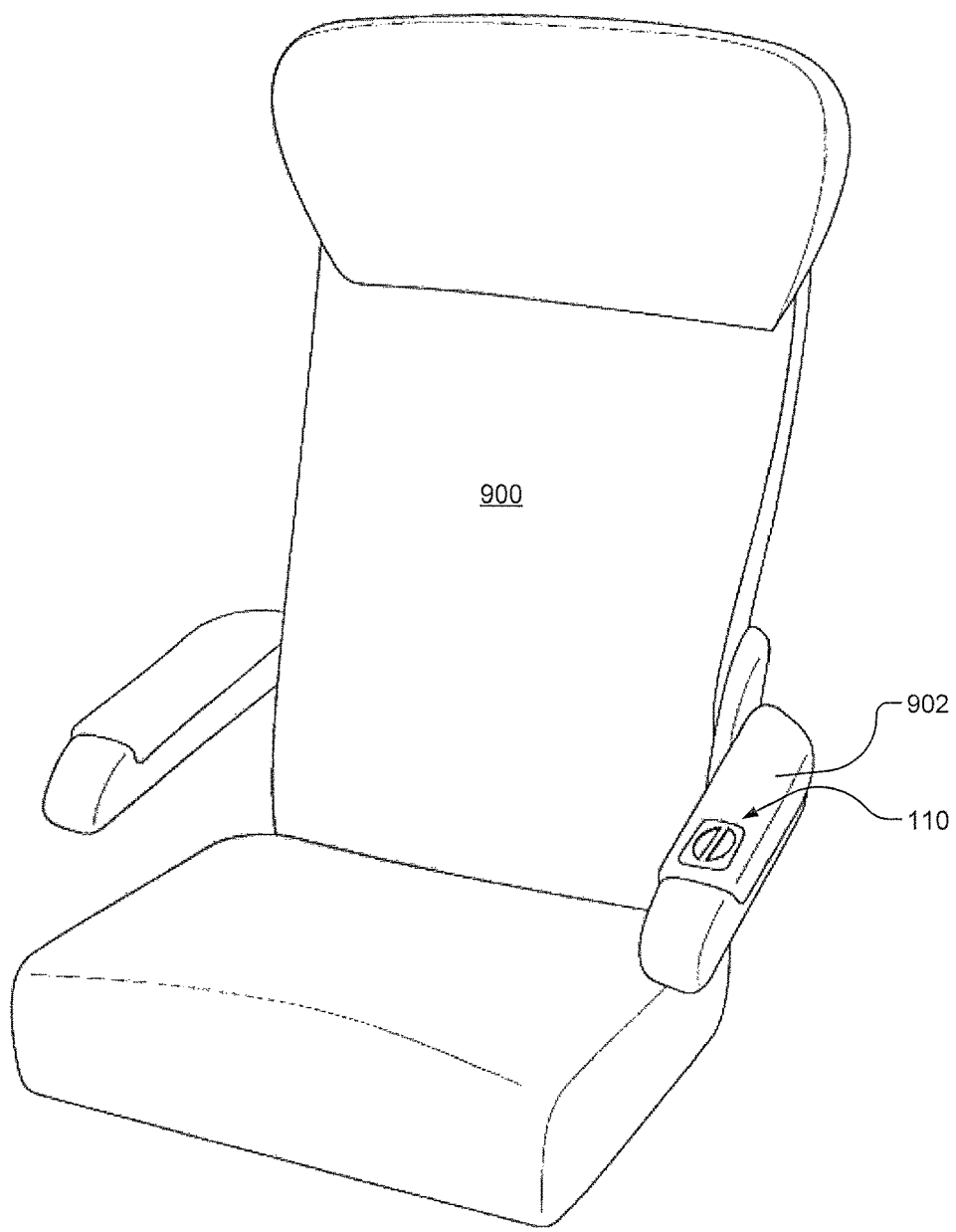
FIG. 9 is a perspective view of an example train seat including a motion sickness mitigation device integrated into the armrest.

Referring now to FIG. 9, an example implementation of the MSMD 110 integrated into an armrest 902 of a train seat 900 is shown. In addition, in some examples, the MSMD 110 may be oriented differently than the orientation shown in FIG. 9. For example, in some implementations, the MSMD 110 may be rotated 90 degrees (either clockwise or counterclockwise) from the orientation depicted in FIG. 9.

Figure 10:
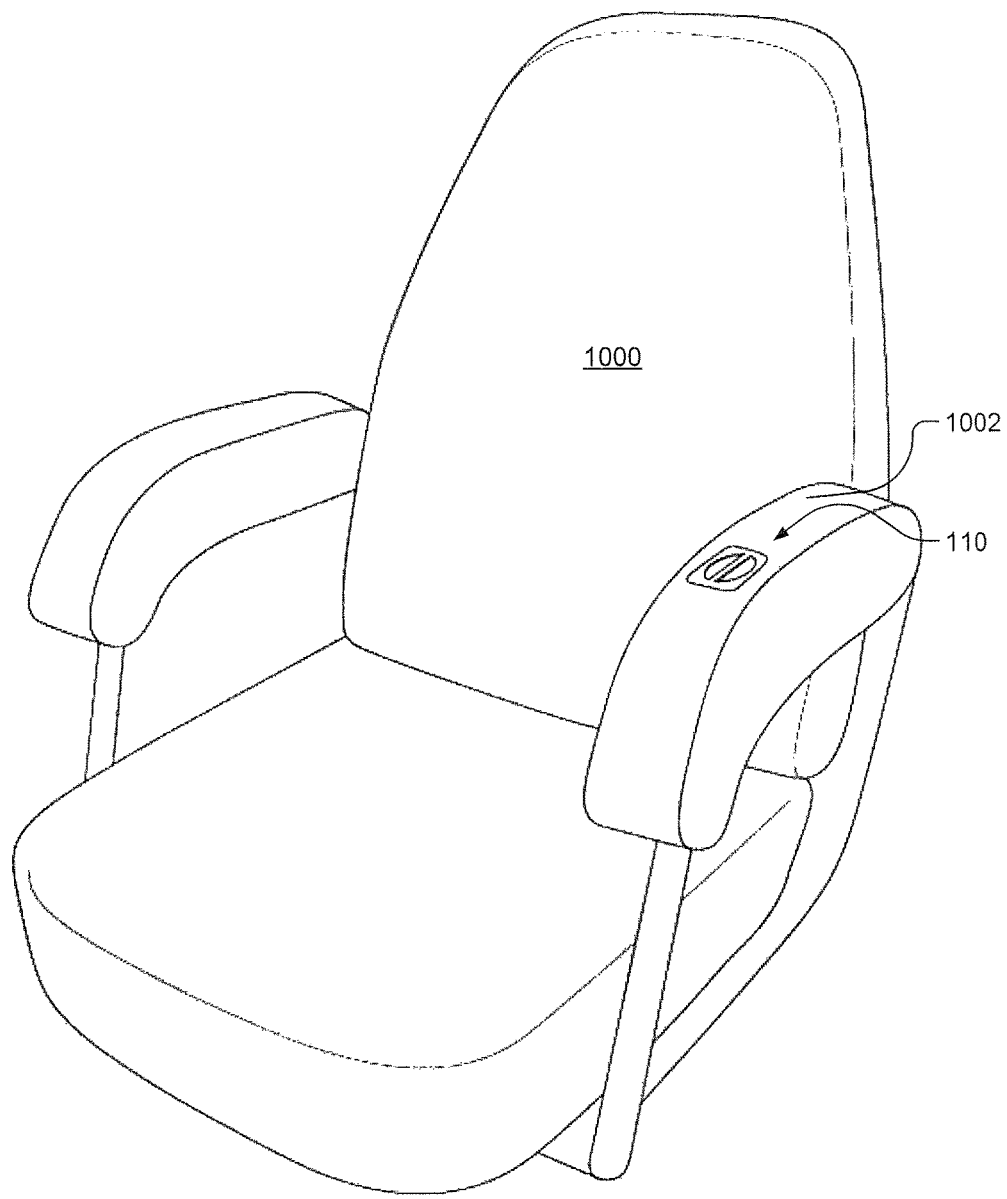
FIG. 10 is a perspective view of an example boat seat including a motion sickness mitigation device integrated into the armrest.

Referring now to FIG. 10, an example implementation of the MSMD 110 integrated into an armrest 1002 of a boat seat 1000 is shown. In addition, in some examples, the MSMD 110 may be oriented differently than the orientation shown in FIG. 10. For example, in some implementations, the MSMD 110 may be rotated 90 degrees (either clockwise or counterclockwise) from the orientation depicted in FIG. 10.

Figure 11:
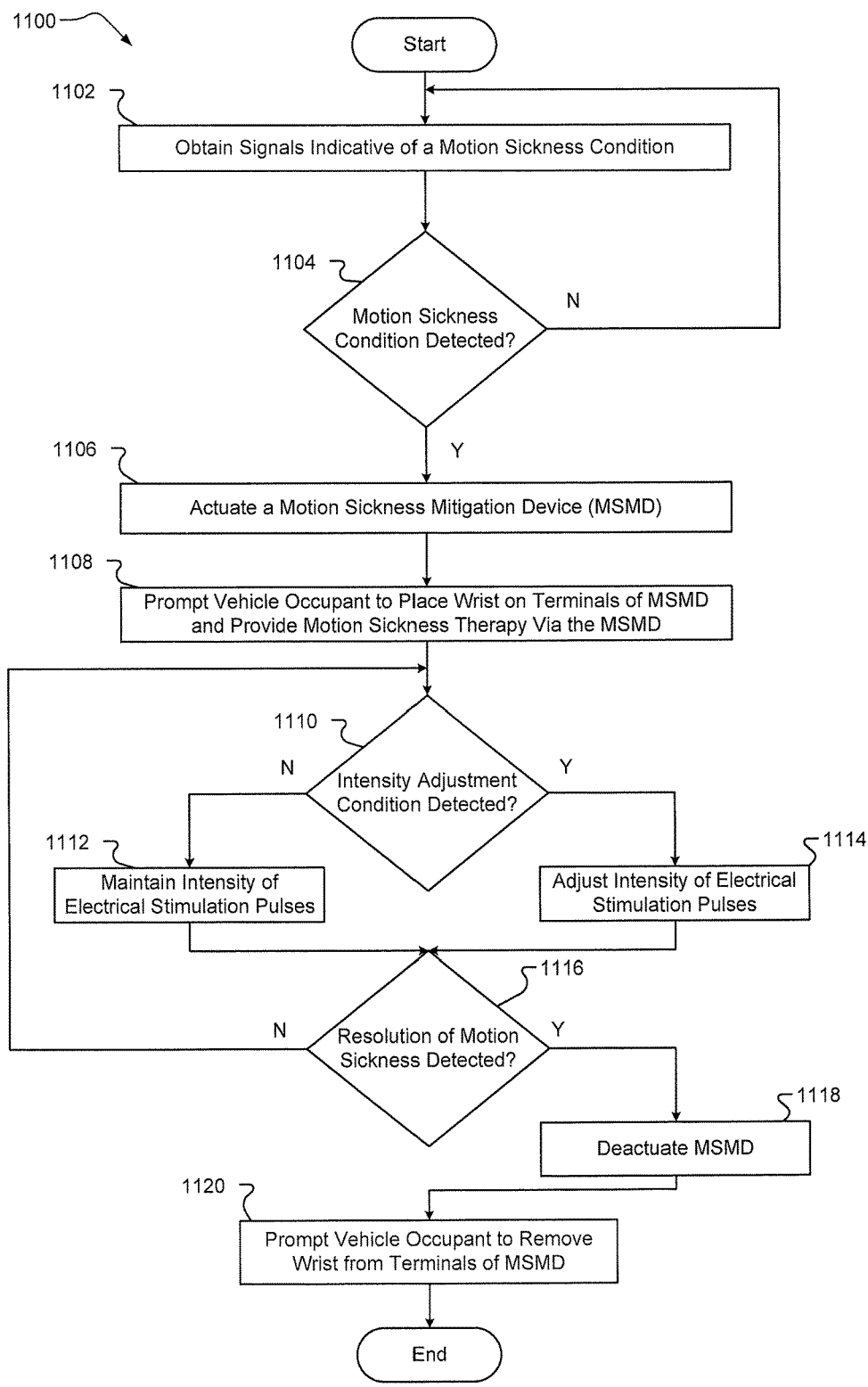
FIG. 11 is a flowchart illustrating an example method for mitigating motion sickness in a vehicle.

Referring now to FIG. 11, a flowchart illustrating an example method 1100 for mitigating motion sickness in a vehicle is provided. The method 1100 begins at 1102 where signals indicative of a motion sickness condition are obtained. At 1104, a determination is made, based on the obtained signals, as to whether a motion sickness condition has been detected. If a motion sickness condition has not been detected, the method 1100 returns to the start. If a motion sickness condition has been detected, the method 1100 continues to 1106 where a MSMD is actuated. At 1108, a vehicle occupant is prompted to place their wrist on the terminals (e.g., electrodes) of the MSMD, and motion sickness therapy is provided via the MSMD. The vehicle occupant may be prompted via a sound (e.g., from speakers of the vehicle) or through a user interface integrated into the vehicle. The therapy may take the form of electrical stimulation pulses administered through the MSMD to the occupant's wrist.

At 1110, a determination is made as to whether an intensity adjustment condition has been detected. Factors that may be considered in determining whether an intensity adjustment condition has been detected include, but are not limited to, a vehicle occupant's weight, a vehicle occupant's reaction to motion sickness therapy (e.g., as measured by a galvanic skin sensor or EEG), and/or user profile information indicating the vehicle occupant's physical characteristics (e.g., age), preferences (e.g., a preferred intensity level and/or frequency of electrical stimulation pulses), and/or historical use data. If an intensity adjustment condition is not detected, the method 1100 proceeds to 1112 where the intensity level of the electrical stimulation pulses is maintained. However, if an intensity adjustment condition is detected, the method 1100 proceeds to 1114 where the intensity of the electrical stimulation pulses is adjusted (i.e., increased or decreased).

At 1116, a determination is made as to whether the vehicle occupant's motion sickness has been resolved. This determination may be made based on, for example, physical characteristics of the vehicle occupant (e.g., reduced temperature, reduced sweating, brain wave patterns disassociated with motion sickness, etc.) as measured by various sensors, or directly from the vehicle occupant via user input (e.g., input into a user interface and or MSMD application). If the vehicle occupant's motion sickness has not been resolved, the method 1100 returns to 1110. However, if the vehicle occupant's motion sickness has been resolved, the method 1100 continues to 1118 where the MSMD is deactuated (e.g., turned off). At 1120, the vehicle occupant is prompted (e.g., via a user interface or sound) to remove their wrist from the terminals of the MSMD and the method 1100 concludes.

Figure 12:
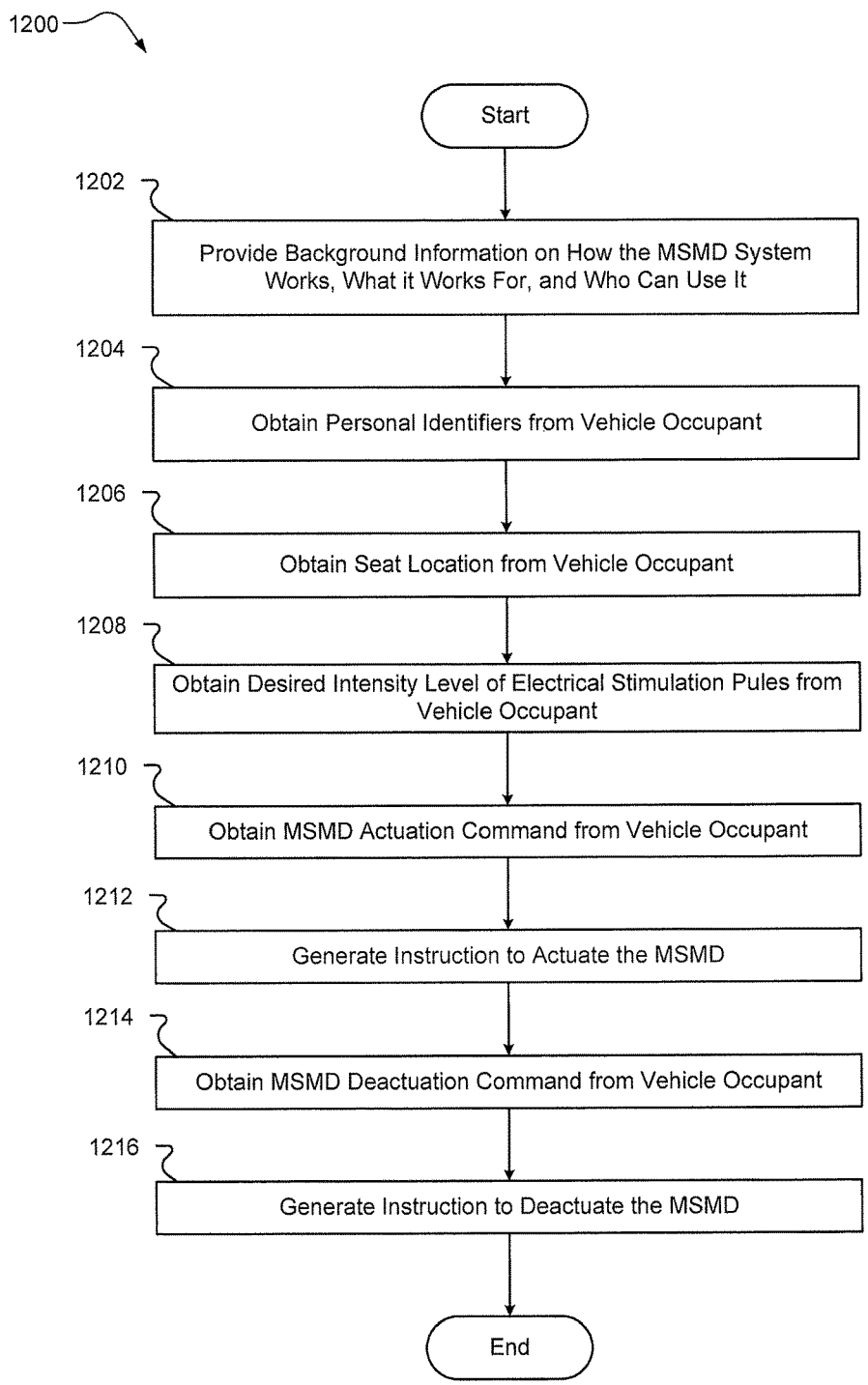
FIG. 12 is a flowchart illustrating an example method for controlling a system for mitigating motion sickness in a vehicle via an application or user interface.

Referring now to FIG. 12, a method 1200 for controlling a system for mitigating motion sickness in a vehicle via an application (e.g., the MSMD application 120) or user interface (e.g., user interface 108) is provided. The method 1200 may suitably be carried out by a user interface alone, an application alone, or some combination of a user interface and application.

The method 1200 begins at 1202 where background information is provided (e.g., visually or audibly) on how the MSMD system works, what it works for (i.e., what symptoms is addresses), and who can use it (e.g., what ages of occupants may suitably use the MSMD system). At 1204, personal identifiers are obtained from the vehicle occupant. At 1206, a seat location for the vehicle occupant is obtained. At 1208, a desired intensity level of electrical stimulation pulses is obtained from the vehicle occupant. At 1210, an MSMD actuation command is obtained from the vehicle occupant. At 1212, an instruction is generated to actuate the MSMD. At 1214, an MSMD deactuation command is obtained from the vehicle occupant. Finally, at 1216, an instruction to deactuate the MSMD is generated and the method 1200 concludes.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules, circuit elements, semiconductor layers, etc.) are described using various terms, including "connected," "engaged," "coupled," "adjacent," "next to," "on top of," "above," "below," and "disposed." Unless explicitly described as being "direct," when a relationship between first and second elements is described in the above disclosure, that relationship can be a direct relationship where no other intervening elements are present between the first and second elements, but can also be an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A.

In this application, including the definitions below, the term "module" or the term "controller" may be replaced with the term "circuit." The term "module" may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

The term code, as used above, may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuit that, in combination with additional processor circuits, executes some or all code from one or more modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more modules.

The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory, tangible computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks, flowchart components, and other elements described above serve as software specifications, which can be translated into the computer programs by the routine work of a skilled technician or programmer.

The computer programs include processor-executable instructions that are stored on at least one non-transitory, tangible computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation) (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

None of the elements recited in the claims are intended to be a means-plus-function element within the meaning of 35 U.S.C. § 112(f) unless an element is expressly recited using the phrase "means for," or in the case of a method claim using the phrases "operation for" or "step for."

What is claimed is:

1. A system comprising:
 a motion sickness mitigation device (MSMD) integrated into a vehicle and configured to generate electrical stimulation pulses upon actuation; and
 a controller operatively connected to the MSMD, wherein the controller is configured to:
 obtain signals indicative of a potential motion sickness condition;

determine whether a motion sickness condition exists based on the signals; and in response to determining that a motion sickness condition exists, actuate the MSMD, wherein the vehicle comprises an automobile and wherein the MSMD is integrated into a face plate of an interior door panel.

2. The system of claim 1, further comprising:

one or more motion sickness detectors operatively connected to the controller and configured to generate the signals indicative of the potential motion sickness condition.

3. The system of claim 2, wherein the one or more motion sickness detectors comprises at least one of: a galvanic skin cell sensor; an electroencephalogram (EEG) sensor; an accelerometer; a speed sensor; a yaw-rate sensor; a tilt-sensor; a GPS system; a clock; a navigation system; and a weather forecast system.

4. The system of claim 1, wherein controller is configured to determine whether the motion sickness condition exists by at least one of:

determining that a vehicle occupant is currently experiencing motion sickness; and determining that the vehicle occupant is likely to experience motion sickness in the future.

5. The system of claim 1, wherein the MSMD comprises electrical stimulation adjustment buttons configured to adjust at least one of: an intensity level of the electrical stimulation pulses and a frequency of the electrical stimulation pulses.

6. A system comprising:

a motion sickness mitigation device (MSMD) integrated into a vehicle and configured to generate electrical stimulation pulses upon actuation;

one or more motion sickness detectors configured to generate signals indicative of a potential motion sickness condition; and a controller operatively connected the MSMD and to the one or more motion sickness detectors, wherein the controller is configured to:

obtain signals indicative of the potential motion sickness condition;

determine whether a motion sickness condition exists based on the signals; and in response to determining that a motion sickness condition exists, actuate the MSMD, wherein the vehicle comprises an automobile and wherein the MSMD is integrated into a face plate of an interior door panel.

7. A system comprising:

a motion sickness mitigation device (MSMD) integrated into a faceplate of an interior door panel of an automobile and configured to generate electrical stimulation pulses upon actuation; and a controller operatively connected the MSMD, wherein the controller is configured to:

obtain signals indicative of a potential motion sickness condition;

determine whether a motion sickness condition exists based on the signals;

in response to determining that a motion sickness condition exists, actuate the MSMD, wherein the MSMD comprises electrical stimulation adjustment buttons configured to adjust at least one of: an intensity level of the electrical stimulation pulses and a frequency of the electrical stimulation pulses.

* * * * *